United States Patent [19]

Mann

[11] 4,199,423
[45] Apr. 22, 1980

[54] HEATED ELECTROLYTE EXHAUST GAS SENSOR AND METHOD OF MAKING IT

[75] Inventor: Gamdur S. Mann, Flint, Mich.

[73] Assignee: General Motors Corporation, Detroit, Mich.

[21] Appl. No.: 963,828

[22] Filed: Nov. 27, 1978

[51] Int. Cl.² .................................... G01N 27/46
[52] U.S. Cl. .................................... 204/195 S
[58] Field of Search .................... 204/15, 195 S

[56] References Cited

U.S. PATENT DOCUMENTS

| 3,546,086 | 12/1970 | Sayles | 204/195 S |
|---|---|---|---|
| 3,815,560 | 6/1974 | Wahl et al. | 123/117 R |
| 3,960,693 | 6/1976 | Weyl et al. | 204/195 S |

FOREIGN PATENT DOCUMENTS 2702432  7/1977  Fed. Rep. of Germany ....... 204/195 S Primary Examiner—T. Tung
Attorney, Agent, or Firm—Robert J. Wallace

[57] ABSTRACT

A readily manufacturable heated solid electrolyte oxygen responsive exhaust gas sensor. An elongated heater is insulatingly supported in subassembly with a tubular reference electrode terminal in desired predetermined disposition relative to the solid electrolyte. The heater has an enlargement intermediate its ends. The heater is coaxially nested within a pair of ceramic sleeves, with the sleeves axially spaced by the enlargement. The sleeves are in turn coaxially disposed within the electrode terminal, and clamped together by inward electrode terminal shoulders, one of which is preferably formed by crimping. The heater enlargement is preferably integrally formed. No special inlet need be provided in the sensor for admission of air when air reference is used.

6 Claims, 5 Drawing Figures

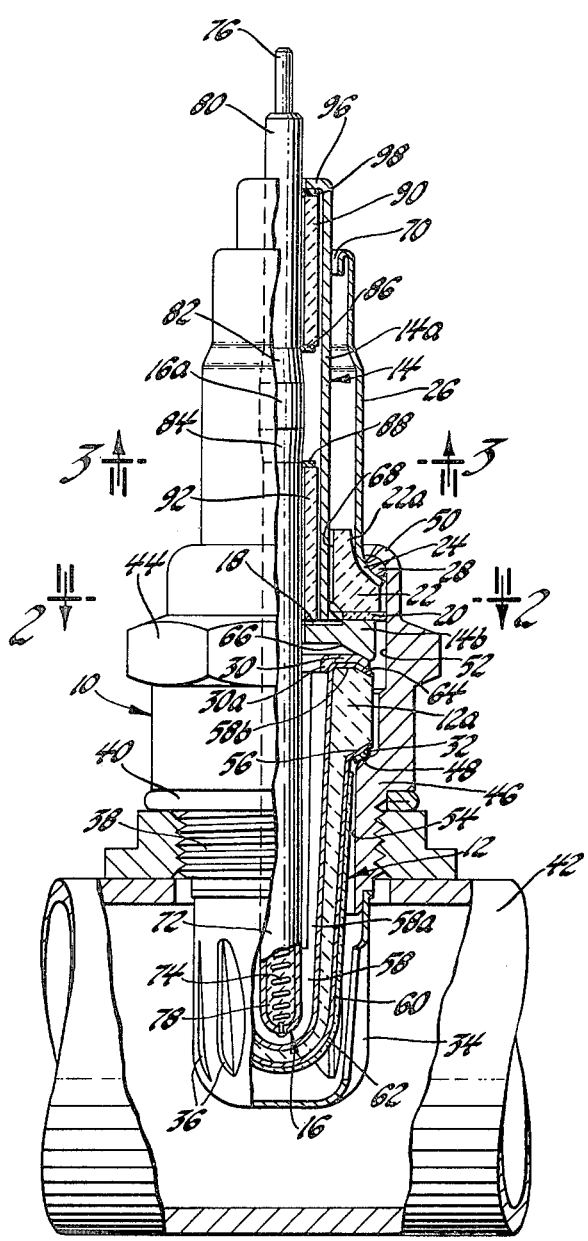
Fig. 1
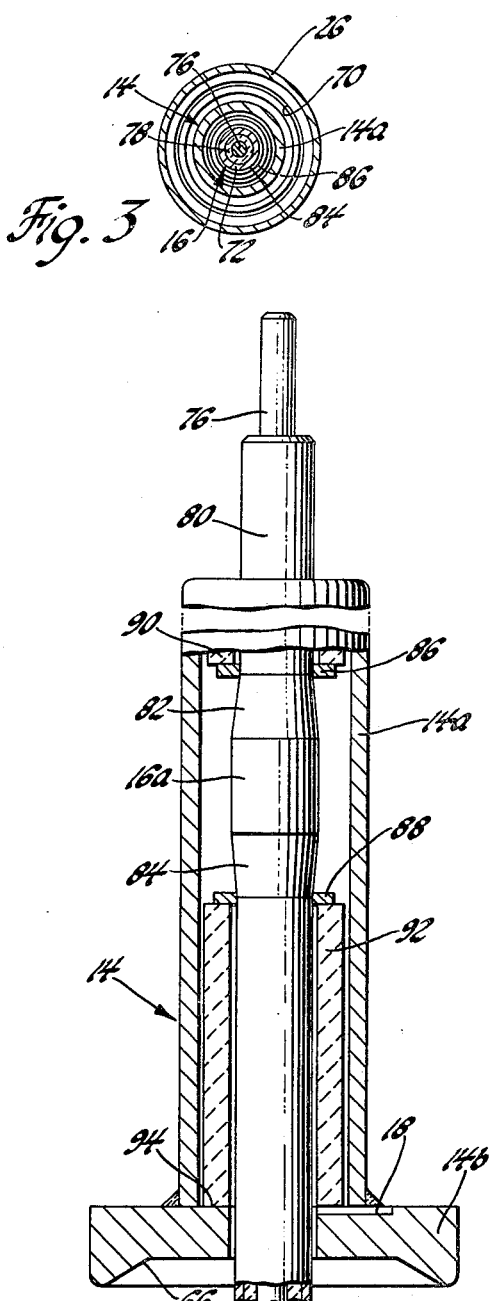
Fig. 3
Fig. 4
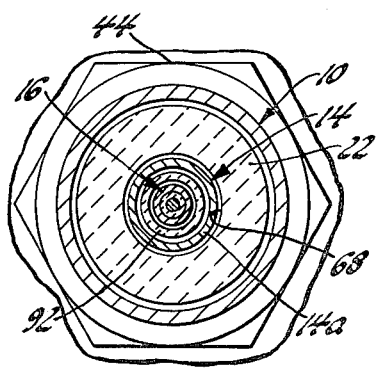
Fig. 2
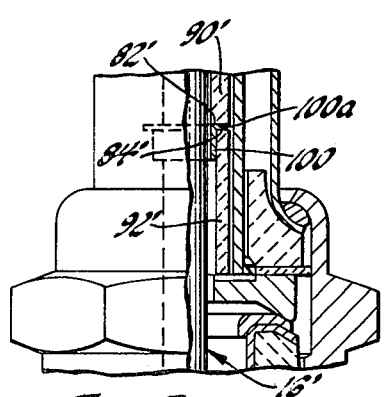
Fig. 5
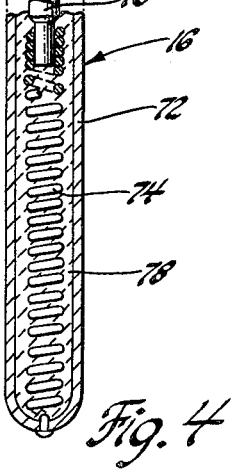

HEATED ELECTROLYTE EXHAUST GAS SENSOR AND METHOD OF MAKING IT

FIELD OF THE INVENTION

This invention relates to a heated galvanic-type solid electrolyte oxygen responsive exhaust gas sensor, and more particularly to an improved readily assemblable heater-electrode terminal subassembly and method of making such a sensor.

BACKGROUND OF THE INVENTION

Solid electrolyte galvanic oxygen sensors essentially include an oxygen ion-conductive ceramic body with porous electrodes on opposite faces of the body. One electrode is exposed to a reference source of oxygen. The other electrode is exposed to a source whose oxygen content is to be measured. A difference in oxygen partial pressure at the electrodes results in a corresponding electrode potential difference, providing a sensor output voltage.

The output voltage of such sensors can be used to measure oxygen or unburned combustibles in combination gases produced by an internal combustion engine. This voltage can be used in monitoring and controlling the combustion process, as disclosed in U.S. Pat. Nos. 3,616,274 Eddy, 3,844,920 Burgett et al and U.S. Ser. No. 787,900 Howarth, filed Apr. 15, 1977.

The sensor solid electrolyte must be at an elevated temperature to obtain an appreciable output voltage. Moreover, sensor output voltage varies with changes in temperature, especially at lower operating temperatures. Combustion gases can be used to heat the sensor to operating temperatures but such gases vary widely in temperature, particularly when from an internal combustion engine. It may be desirable in some applications to include a heater in the sensor. For automotive applications, the heated sensor should be particularly rugged and reliable. In addition, for higher reliability and lower cost, the heated sensor should be simple and readily manufacturable. United States Patent application Ser. No. 892,644, entitled "Heated Solid Electrolyte Oxygen Sensor" filed Apr. 3, 1978, in the name of M. P. Murphy, discloses forming a subassembly of the heater and the sensor reference, i.e. air, electrode terminal. In the subassembly, the heater is prealigned on the electrode terminal. The electrode terminal contacts the reference electrode in a predetermined alignment. When the reference electrode terminal-heater subassembly is assembled with its solid electrolyte, the heater is thus also inherently aligned with the solid electrolyte. The heater-electrode terminal subassembly approach is particularly useful for adding a heater to the oxygen sensor disclosed in U.S. Pat. No. 3,844,920 Burgett et al.

An elongated heater is insulatingly supported on the reference electrode terminal in a particularly unique manner that is described and claimed in United States patent application Ser. No. 892,642, entitled "Solid Electrolyte Oxygen Sensor with Electrically Isolated Heater", filed Apr. 3, 1978, in the names of M. P. Murphy and R. D. Willis. In this latter invention the elongated heater is supported by a vitrified bond within at least one ceramic sleeve that is, in turn, supported by a vitrified bond within the tubular portion of the reference electrode terminal. Means coacting with terminal and housing flanges hold the electrolyte member, heater-terminal subassembly and housing in a fixed predetermined concentric relationship. Precise alignment is assured, even though the components are readily assemblable. The vitrified bond can provide a simple, rugged, reliable and readily manufacturable subassembly for a heated oxygen sensor in which the heater is electrically isolated from the sensor electrodes.

On the other hand, affixing the elongated heater to the ceramic sleeve and electrode terminal by a vitrified bond requires a furnace treatment of the subassembly. Furnace treatments can be costly in that they are slow and require extensive plant floor space. Energy consumption can be expensive too. Also, glass bonding may not be as rugged or reliable as may be desired for severe circumstances. I have found how the heater can be insulatingly supported on the electrode terminal without need for a fused glass bond. I have found how to mechanically support the heater on the electrode terminal, and still keep the two electrically and thermally isolated. In a preferred sensor and method of making it, the elongated heater has a swaged cylindrical metal sheath. The sheath has an enlargement intermediate its ends that is integrally formed while the sheath is being swaged. The enlargement provides a mechanical interlock with the ceramic sleeves for mechanically affixing the heater to the electrode terminal by a simple, rapid and rugged crimping operation.

SUMMARY OF THE INVENTION

This invention involves a coaxial cylindrical galvanic oxygen responsive exhaust gas sensor having a tubular metal shell for enclosing a cup-shaped electrolyte member. The sensor also has an electrode terminal tube coaxially disposed within the shell and contacting an upper edge on the electrolyte member. The heater is insulatingly and coaxially supported within the terminal tube. The heater-terminal tube subassembly includes a pair of aligned similar ceramic sleeves coaxially disposed within the terminal tube and extending along a substantial length of it. The heater is coaxially disposed within the ceramic sleeves. The heater has a conformation intermediate its ends that engages facing ends on the sleeves. Opposed sleeve ends are clamped together by opposed inward shoulders on the electrode terminal. In a preferred embodiment the outer conformation on the heater is formed during swaging of an outer metal sheath on the heater, and at least one of the terminal tube shoulders is formed by crimping.

BRIEF DESCRIPTION OF THE DRAWING

Other features and advantages of the invention will become more apparent from the following description of preferred embodiments thereof and from the drawing, in which:

FIG. 1 shows an elevational view in partial section of an oxygen sensor made in accordance with this invention;

FIG. 2 shows a sectional view along the line 2—2 of FIG. 1;

FIG. 3 shows a sectional view along the line 3—3 of FIG. 1;

FIG. 4 shows an enlarged sectional view in partial elevation of the heater-electrode terminal subassembly in the sensor shown in FIGS. 1-3; and FIG. 5 shows a fragmentary elevational view in partial section of another embodiment of a heated oxygen sensor made in accordance with this invention.

DESCRIPTION OF THE PREFERRED EMBODIMENTS

FIGS. 1-4 show a tubular metal shell 10, a solid electrolyte tube 12 that is closed at its bottom end, an electrode terminal member 14, and a heater 16. The electrolyte tube can be of zirconia, thoria, or the like, that is partially or fully stabilized in its cubic crystalline form. Zirconia containing 4-8 mole percent yttria can be used. Electrode terminal member 14 has a central tubular portion 14a circumferentially welded at its lower end to the upper surface of a coaxial annular member to provide a circumferential outward flange 14b normal to the axis of tube 14a. The annular member has a groove 18 in its upper surface, to provide an air passage under the lower end of tube 14a. Heater 16 is coaxially supported within terminal tube 14a, and forms a subassembly therewith in which heater 16 is electrically isolated from terminal member 14. The subassembly is specifically illustrated in FIG. 4, and will hereinafter be described in further detail.

A flat mica washer 20 is disposed on the upper surface of flange 14b. A ceramic ring 22 is concentrically disposed on mica washer 20 around terminal tube 14a. Ceramic ring 22 has an upward, decreasing taper 22a on its outer surface. A flared lower end 24 of a tubular, upper metal shield 26 nests on the tapered outer surface 22a of ceramic ring 22. An annular metal gasket 28 surrounds the flared lower end 24 of shield 26. Below terminal flange 14b is an upper metal sealing ring 30, a circumferential flange 12a around the open upper end of the electrolyte tube 12, and metal lower sealing ring 32. A cup-shaped lower metal shield 34 is affixed to the lower end of shell 10, surrounding the otherwise exposed lower end of electrolyte tube 12. Lower metal shield 34 has louvers 36, for entry of exhaust gases. All of the aforementioned elements are coaxially aligned.

The sealing rings 28 and 30 can be of any soft metal, such as copper or nickel. The shell 10, metal shields 26 and 34, and at least the outer covering of heater 16 are made of metal which will withstand the conditions of sensor use, as for example stainless steel and preferably a nickel-based alloy. Ceramic ring 22 can be of any suitable ceramic, as for example alumina. Annular metal gasket 28 can be of soft steel.

On its outer surface, tubular metal shell 10 has circumferential threads 38 for mounting the sensor in an automobile exhaust pipe 42. Above threads 38 is an outer annular soft steel gasket 40. Above gasket 40 is a circumferential hexagonal array of surface flats 44 for tightening shell 10 in the exhaust pipe 42. If desired, the sensor could be alternatively mounted in an exhaust system manifold, tailpipe, or special parallel exhaust passage.

On its inner surface, shell 10 has lower inward circumferential flange 46, providing an annular sloped shoulder 48. Shoulder 48 forms a tapered seat, on which lower sealing ring 32 is disposed. The upper end of shell 10 has an inward circumferential flange 50, formed by crimping or rolling over the soft steel gasket 28. Sloped shoulder 48 and upper flange 50 cooperate to concentrically clamp the aforementioned flanges, rings and washers within shell 10 in a predetermined fixed relationship.

The inner surface of shell 10 is generally cylindrical. Above sloped shoulder 48 it has a larger diameter portion 52 and a smaller diameter portion 54. Portion 52 is of larger diameter to radially space shell 10 from the outer periphery of electrode terminal flange 14b, for electrical isolation purposes. Portion 54 is of a diameter only slightly larger than the outer diameter of the adjacent electrolyte tube flange 12a. The adjacent tube and shell diameters are sufficiently close to provide substantial coaxial alignment but not so close as to prevent easy assembly. About one millimeter or less nominal differences may be suitable.

Solid electrolyte tube 12 is tapered from its upper end to its closed lower end. The upper end has a larger diameter portion that forms a circumferential circular concentric flange 12a. Wall thickness on electrolyte tube 12 gradually decreases from flange 12a to the tube lower end. Flange 12a has a lower surface 56 which forms a sloped shoulder generally similar in slope to shoulder 48 of shell 10. Shoulders 48 and 56 cooperate, along with the shell reduced diameter portion 54, to coaxially align electrolyte tube 12 within shell 10. Lower metal sealing ring 32 between shoulders 48 and 56 provides a gas tight seal, and low resistance electrical communication between the contacting surfaces of tube 12 and shell 10.

A first porous thick film platinum electrode 58 fully covers the bottom inner surface of electrolyte tube 12. This inner electrode 58 serves as a reference electrode, in this case an air electrode, for the sensor. A conductive strip-like coating 58a extends up the tube inner surface from electrode 58 to the open end of the tube 12, where it intersects with conductive coating 58b on the end face of electrolyte tube 12. Conductive coating 58b can merely be a stripe across the end face of electrolyte tube 12 or be a continuous circumferential coating. The platinum electrode 58 and conductive coatings 58a and 58b can be a continuous layer formed by brishing on a platinum paste and then firing it, as is usual.

A second porous thick film platinum electrode 60 covers the entire outer surface of tube 12, including the shoulder 56, below flange 12a. This outer electrode 60 serves as the exhaust gas electrode for the sensor. Outer platinum electrode 60 can be formed in the same manner as inner electrode 58. However, it may be more desirable to apply it by evaporation, chemical vapor deposition, sputtering or other such techniques. Outer electrode 60 is in low resistance electrical contact with shell 10 through the lower soft metal gasket 32. Hence, this electrode is also in low resistance electrical communication with upper shield 26 and exhaust pipe 42. A porous ceramic coating 62 of alumina, spinel, or the like preferably covers the outer electrode 60 below electrolyte tube shoulder 56.

The upper end of electrolyte tube 12 is chamfered on its periphery, forming a sloped shoulder 64. The outer periphery of upper sealing ring 30 has a complementary contour. The inner periphery of sealing ring 30 has an axial flange 30a to facilitate concentric seating of sealing ring 30 on the open end face of tube 12. Inner electrode 58 and electrode terminal 14 are in low resistance electrical contact through platinum strip 58a, conductive coating 58b and sealing ring 30. Electrode terminal flange 14b has a sloped shoulder 66 on the outer periphery of its lower face, at least generally corresponding to sealing ring 30 and electrolyte tube shoulder 64. Sloped shoulders 64 and 66 cooperate to coaxially align electrode terminal 14 with electrolyte tube 12.

The upper surface of flange 14b is normal to the axis of terminal tube 14a. Also, the lower end face of ceramic ring 22 is normal to the longitudinal axis of coaxial bore 68 extending through the ceramic ring. The tapered outer surface 22a of ceramic ring 22 coacts with the adjacent metal gasket 28 and shell flange 48 to not only clamp the components together but also coaxially align ceramic ring 22 and its bore 68 within shell 10. Bore 68 has a diameter about one millimeter, preferably about 0.1-0.2 millimeter larger than the outer diameter of terminal tube 14a, enhancing coaxial alignment of terminal 14 and the subassembly of which it is a part. As can be seen, the taper 22a on ceramic ring 22 is gradual at its upper end to enhance coaxial alignment and more abrupt at its lower end to enhance the clamping effect. Since flared lower end 24 of upper metal shield 26 conforms to the taper 22a of the ceramic ring and nests thereon under gasket 28, shield 26 is also coaxially aligned.

The upper end 70 of shield 26 is open and radially spaced from heater 16. Shield 26 is, therefore, electrically isolated from terminal 14 and heater 16. While not shown, shield 26 can have a conformation above ceramic ring 22 to retain an upper insulating spacer in place and help retain a terminal connector that may be attached. As mentioned, shield 26 is in low resistance electrical communication with outer electrode 60 on electrolyte tube 12. Shield 26 can, therefore, serve as a ground connection, if desired, instead of exhaust pipe 42. To insure low resistance connection, an electroplated coating (not shown) of silver or the like can be provided around the upper end of shield 26.

As can be seen better in FIG. 4, heater 16 includes a tubular outer metal sheath 72 closed at its lower end, where a helical heating coil 74 is coaxially disposed therein. The upper end of coil 74 is welded to a coaxial inner rod 76. Coil 74 and rod 76 are spaced from outer sheath 72 by ceramic insulation 78 as for example powdered magnesia. If desired, the open upper end 80 of sheath 72 can be closed by means of a sealing ring (not shown) of nonconductive material, as for example silicone rubber. The upper end 80 of sheath 72 can have a silver coating (not shown) as can the adjacent outer portion of inner heater rod 76, to insure low resistance electrical connections thereat. Heater 16 is actuated by applying an electrical potential across sheath 72 and rod 76. Analogously, the upper ends of terminal tube 14a and shield 26 can be silver plated (not shown) to enhance obtaining low resistance electrical connections thereto. Thus, a sensor is provided with four discrete coaxial terminal connections.

Heater 16 is preferably made in accordance with the teachings of U.S. Pat. Nos. 2,898,571 Moule et al and 3,252,122 Baxter. The heater 16 is formed by initially placing a heater coil 74 and inner rod 76 within a cylindrical outer sheath 72 that is closed at one end. One end of the coil is welded to the bottom of the sheath and the other to the end of the rod. A ceramic insulation is then placed in the sheath 72 as a sleeve or as powder to radially space the rod and coil from the sheath. The resultant assembly is then swaged to reduce its diameter and rigidly interlock the heater assembly. The ceramic insulation is densely packed around the rod and coil during swaging and the spacing from the outer sheath is maintained. During swaging, the axial length of the sheath 72 and rod 76 increases. In most instances, the heater sheath 72 will be swaged in such a manner as to retain the original cylindrical configuration of sheath 72. In this invention, I prefer that a portion of the sheath 72 intermediate the sheath ends not be swaged as severely as end portions. In some instances, it may even be desirable not to swage this intermediate portion at all. The middle portion which is not swaged as severely forms an integral conformation 16a intermediate the ends of heater 16 which provides oppositely facing upper and lower shoulders 82 and 84 on the outer surface of heater 16.

The upper end of heater 16 coaxially extends through a first flat metal washer 86, which engages the upper shoulder 82. The lower end of heater 16 extends coaxially through a second flat metal washer 88 which engages with the lower shoulder 84. Washers 86 and 88 can be of stainless steel and are identical in size. They respectively provide a circumferential flange with opposed faces on heater 16. The opposed faces provide opposite axially facing shoulders. Because of heater enlargement 16a, washers 86 and 88 are axially locked in place on heater 16 when under compression.

Above conformation 16a, the heater 16 is coaxially disposed within an upper ceramic sleeve 90. Below conformation 16a, heater 16 is coaxially disposed within a lower ceramic sleeve 92. Sleeves 90 and 92 are in turn coaxially disposed within tubular portion 14a of electrode terminal 14. Ceramic sleeves 90 and 92 can be of alumina and are identical in composition and size. Ceramic sleeves 90 and 92 extend substantially along the entire length of terminal tube 14a. They not only electrically but thermally separate heater 16 from terminal tube 14a. The inner diameter is only slightly larger than the outer diameter of the cylindrical portion of sheath 72, sufficient to permit easy assembly. Analogously, the outer diameter of ceramic sleeves 90 and 92 is only slightly less than the inner diameter of terminal tube 14a, sufficient to permit easy assembly. When assembled as shown in FIG. 4, the heater 16, washers 86 and 88 and ceramic sleeves 90 and 92 will be coaxial with the terminal tube 14a. As previously mentioned, terminal tube 14a is normal to terminal flange 14b. For best alignment, tube 14a is at least five times longer and preferably more than 10-15 times longer, than the dimension of its inner diameter. Consequently, heater 16 is normal to terminal flange 14b.

Tubular portion 14a has a larger inner diameter than flange 14b, which provides an inner circumferential shoulder 94 at the lower end of tube 14a. Shoulder 94 supports the lower end of ceramic sleeve 92, which in turn supports lower washer 88. Washer 88 supports heater 16 by engagement with lower heater shoulder 84. The heater is clamped against lower shoulder 94 by an upper shoulder 96. Shoulder 96 is provided by rolling or crimping the upper end of terminal tube 14a over a silicone rubber ring 98. Ring 98 in turn abuts the upper end of upper ceramic sleeve 90. The lower end of upper sleeve 90 abuts washer 86, which in turn engages upper heater shoulder 82 to clamp the heater 16 in place and lock the terminal tube and heater together as a rigid, rugged assembly. Normal and accepted crimping and rolling processes can be used to form the upper shoulder 96.

The inner diameter of terminal flange 14b is preferably about 0.2-0.4 millimeter larger than the inner diameter of ceramic sleeve 92 and 94. This will insure a spacing and electrical isolation between sheath 72 and terminal flange 14b. Analogously, the upper end of terminal tube 14a is only crimped over the silicone rubber ring 98 sufficiently to lock the assembly together but so much as to bring terminal tube 14a into contact with sheath 72. Otherwise, terminal 14 and heater 16 would be electrically connected. Still further, flat circular washers 86 and 88 have an inner diameter which is only slightly larger than that of the upper and lower ends of cylindrical sheath 72. The outer diameter of washers 86 and 88 is about 0.2-0.4 millimeter less than the outer diameter of ceramic sleeves 90 and 92. Thus, electrical isolation between heater 16 and terminal 14 is maintained.

A baffled air passage between the inner electrode 58 is provided. Air enters the sensor through the annular opening 70 at the upper end of upper shield 26. It passes down between electrode 14 and shield 26 to ceramic ring 22. A generous clearance of about 0.1 millimeter between terminal tube 14a and the axial bore 68 through ceramic ring 22 provides an annular air flow path along tube 14a through bore 68. Below ceramic ring 22, air passes beneath tube 14a to sheath 72 of heater 16 through the groove 18 in the upper face of terminal flange 14b. As previously mentioned, sheath 72 and the inner diameter of flange 14b are spaced about 0.2-0.4 millimeter apart, which inherently provides an annular flow path therebetween. Air passes down along heater 16 into contact with electrode 58. Thus, the interior of the electrolyte tube 12 communicates with the outside air through a baffled passage protecting it from particular contaminants, water splash, etc. It should be emphasized that the respective annular passages within the sensor are formed by merely appropriately dimensioning respective parts with a generous manufacturing clearance. No intricate machining is required and assembly is relatively simple. Accordingly, axial bore 68 of ceramic ring 22 can not only coact to coaxially align the heater-terminal subassembly, but also provide s passage for air flow into the sensor interior.

It should be noted that washers 86 and 88 could be omitted if shoulders 82 and 84 could provide opposed faces normal to the axis of heater 16. Washers 86 and 88, however, appear to be necessary in providing a good mate with end surfaces on ceramic sleeves 90 and 92 if normal manufacturing procedures and tolerances are used. It also should be noted that the principles of this invention can be used to analogously mount the exposed coil-type of heater described and claimed in the United States patent application D-2,424, entitled "Heated Solid Electrolyte Oxygen Sensor", filed in November, 1978 in the names of G. S. Mann et al and assigned to the assignee of this invention. A heated sensor is disclosed in which a resistance heating element is helically wound around a cylindrical ceramic tube. An outer terminal for one end of the coil is crimped around the mandrel to provide a coaxial outer terminal. A coaxial metal rod in ceramic tube provides a coaxial inner terminal for the other end of the heating coil. An enlargement on the ceramic tube could be provided intermediate the tube ends that is analogous to conformation 16a on the heater 16 of this invention. In the alternative, a flangelike conformation could be provided in the terminal that is crimped around the ceramic tube. Either or both can be used to provide oppositely facing shoulders on the heater corresponding to upper and lower shoulders 82 and 84 in FIGS. 1-4 hereof.

Also, sleeves 90 and 92 need not be identical in composition or length. It may be desired, for example, to use a longer cylinder for the ceramic sleeve below conformation 16a, and a shorter insulating annulus above it, such as merely a silicone rubber ring or a mica washer. It may be desirable to include one or more coaxial mica washers somewhere in the series of flanges and shoulders for thermal compensation, as for example is done in the aforementioned U.S. Pat. No. 3,844,920 Burgett et al.

The principles of this invention can also be used with a swaged heater that has no integral enlargement along its length. In such instance, the heater is perfectly cylindrical. A mounting arrangement for such a heater is shown in FIG. 5. In FIG. 5, a flanged ring is welded to the outer surface of a perfectly cylindrical swaged heater 16' at its ends. Swaged heater 16' is identical to the swaged heater 16 in FIGS. 1-4, except that it is perfectly cylindrical. In other words, it does not have the enlarged integral conformation 16a along its length. Flanged ring 100 is welded to heater 16' at a point along its length generally corresponding to conformation 16a. The flange 100a on ring 100 is normal to the heater axis and extends completely around the heater circumference. It thus provides an upper and lower shoulders 82' and 84' for abutment with facing ends on a ceramic sleeve 90' and 92'. Shoulders 82' and 84' of FIG. 5 are quite close together, as compared to shoulders 82 and 84 of FIGS. 1-4 hereof. Ceramic sleeves 90' and 92' are correspondingly longer than sleeves 90 and 92 and thus provide a somewhat better thermal barrier than an equally thick sleeve in FIGS. 1-4. Also the inner diameter of lower ceramic sleeve 92' is slightly larger than upper ceramic sleeve 90', to accommodate the thickness of ring 100, as for example 0.2-0.4 millimeter. Otherwise, the sensor illustrated in connection with FIG. 5 is identical with the sensor shown in FIGS. 1 through 4.

The embodiments of the invention in which an exclusive property or privilege is claimed are defined as follows:

1. In a coaxial cylindrical galvanic oxygen responsive exhaust gas sensor having a metal shell, a solid electrolyte member, an electrode terminal tube and heater subassembly, said shell, electrolyte member, and subassembly being coaxially assembled, the improvement wherein the subassembly includes a pair of annular members coaxially disposed between the heater and terminal tube for thermal and electrical separation and for alignment of the heater in the terminal tube, axially opposed shoulders on said heater for interlock with said annular members, facing internal shoulders on said terminal tube for coaction with said heater shoulders through said annular members, whereby said heater is insulatingly coaxially interlocked in subassembly with said terminal tube.

2. In a coaxial cylindrical galvanic oxygen responsive exhaust gas sensor having a metal shell, a solid electrolyte member, an electrode terminal tube and heater subassembly, said shell, electrolyte member, and subassembly being coaxially assembled, the improvement including at least two axially displaced ceramic sleeves coaxially aligned within and extending along a substantial length of said terminal tube, an elongated heater coaxially disposed in said sleeves, with heater ends outwardly displaced from sleeve and tube ends, oppositely facing axial shoulders on said heater for engagement with facing sleeve ends, and facing internal axial shoulders on said terminal tube for engagement with the other sleeve ends to insulatingly interlock said heater, sleeves and terminal tube in predetermined coaxial disposition.

3. In a coaxial cylindrical galvanic oxygen responsive exhaust gas sensor having a metal shell, a closed ended tubular solid electrolyte member, and a heater-reference electrode terminal tube subassembly, said shell, electrolyte member, and subassembly being coaxially assembled, the improvement including at least two axially displaced ceramic sleeves coaxially aligned within and extending along substantially all of said terminal tube, said terminal tube is over five times longer than its inner diameter, said heater is coaxially aligned in said subassembly by sleeves and thereby radially spaced from the terminal tube, heater ends are displaced outward from the terminal tube and sleeve ends, a swaged outer metal sheath on said heater extending along substantially its entire length, at least one radial circumferential flange affixed to said outer metal sheath for providing oppositely facing heater support shoulders normal to said sheath, said flange having an outer diameter less than the outer diameter of said sleeves, said shoulders abutting facing sleeve ends, the opposite end of one ceramic sleeve abutting an internal shoulder on said terminal tube, the opposite end of the other ceramic sleeve abutting a resilient ring, a portion of the terminal tube crimped over said ring to clamp said heater and ceramic sleeves together in insulating coaxial subassembly with said terminal tube.

4. In a coaxial cylindrical galvanic oxygen responsive exhaust gas sensor having a metal shell, a closed ended tubular solid electrolyte member, and a heater-reference electrode terminal tube subassembly, said shell, electrolyte member, and subassembly being coaxially assembled, the improvement wherein at least two axially displaced substantially equal diameter ceramic sleeves are coaxially disposed within and extend along a substantial length of said terminal tube, a swaged metal sheath encloses said heater, said sheath is substantially cylindrical except for an enlarged circumferential portion intermediate its ends, said enlargement generally provides oppositely facing integral interlock shoulders on said heater, coaxial washers on said heater abut said shoulders on opposite ends of said enlargement, facing ends on said sleeves abut said washers, said washers have an outer diameter less than the outer diameter of said sleeves, the terminal tube has an interior shoulder at its end adjacent said electrolyte member, an opposite end on one of said sleeves abuts said interior shoulder, a resilient coaxial ring abuts the opposite end of the other ceramic sleeve, and the terminal tube is crimped over said ring to insulatingly interlock said heater on said terminal tube in predetermined coaxial disposition.

5. In a method of making a coaxial cylindrical galvanic oxygen responsive exhaust gas sensor having a metal shell, a solid electrolyte member and an elongated heater-reference electrode terminal tube subassembly, the improvement comprising forming said heater with axially opposed integral shoulders intermediate its ends, coaxially disposing the heater within a pair of axially spaced sleeves that interlock with said integral shoulders, coaxially disposing the sleeves and heater within the terminal tube to insulatingly space said heater from said terminal tube, and crimping the terminal tube adjacent at least one outer end of said sleeves to interlock said sleeves and heater in said terminal tube and form a subassembly having an electrically isolated heater in fixed predetermined relationship with said terminal tube, and assembling said subassembly with said electrolyte member and said shell to coaxially align said heater with said solid electrolyte.

6. In a method of making a coaxial cylindrical galvanic oxygen responsive exhaust gas sensor having a metal shell, a circular solid electrolyte member, an electrode terminal tube, and an elongated heater having a swaged outer metal sheath, wherein the heater is insulatingly coaxially affixed within the terminal tube in subassembly therewith, the improvement comprising simultaneously forming axially opposed integral shoulders on said heater outer metal sheath while it is being swaged, machining an internal shoulder at one end of the terminal tube for abutment with an outer end of a ceramic sleeve, coaxially disposing a first ceramic sleeve within the terminal tube in engagement with said shoulder, coaxially disposing a washer on the other end of said sleeve, coaxially disposing said heater within said first washer and first sleeve with one of said heater integral shoulders engaging said washer, coaxially placing a second washer around said heater in engagement with the other heater shoulder, coaxially disposing a second ceramic sleeve around said heater with one end of said sleeve in engagement with said second washer, coaxially disposing an elastomeric ring around said heater with said ring engaging the other end of said second ceramic sleeve, crimping said electrode terminal tube over said ring to form an insulated heater-electrode terminal subassembly, and assembling said subassembly with said electrolyte member and said shell to align said heater with said electrolyte member.

* * * * *